United States Patent [19]

Arias

[11] Patent Number: 4,675,313

[45] Date of Patent: Jun. 23, 1987

[54] PYRETHROID-CONTAINING PHARMACEUTICAL COMPOSITIONS

[75] Inventor: Jose A. Arias, Mexico City, Mexico

[73] Assignee: T & R Chemicals, Inc., Clint, Tex.

[21] Appl. No.: 777,299

[22] Filed: Sep. 18, 1985

Related U.S. Application Data

[63] Continuation-in-part of Ser. No. 595,360, Mar. 30, 1984.

[30] Foreign Application Priority Data

Mar. 31, 1983 [GB] United Kingdom ............... 8308974

[51] Int. Cl.$^4$ ...................... A61K 37/00; A61K 31/01
[52] U.S. Cl. ..................................... 514/65; 514/762; 514/894; 514/934
[58] Field of Search ................. 514/65, 888, 894, 934, 514/762

[56] References Cited

U.S. PATENT DOCUMENTS 4,100,297  7/1978  Grandadom et al. ............... 514/520

FOREIGN PATENT DOCUMENTS 447949  5/1936  United Kingdom.
2072013  9/1981  United Kingdom.

OTHER PUBLICATIONS

Chem. Abst. 80:30695z.
Chem. Abst. 87:111394x.
Chem. Abst. 96:159266v.
Chem. Abst. 98:119212j.
Chem. Abst. 98:149467p.
Bezanger-Beauquesne, Plantes Medicinales, 1969, Tome III, 4, pp. 296–309.
Bezanger-Beauquesne, Tome XVI, 3, pp. 206–229, 1982.
Chem. Abst. 74:102985y.
Chem. Abst. 75:725464.
Chem. Abst. 87:119955r.
Chem. Abst. 53:4570e.
Bezanger-Beauquesne et al, 1980, pp. 390–391, Plantes Medicinales des Regions Temperees.

*Primary Examiner*—Johnnie R. Brown
*Assistant Examiner*—John W. Rollins, Jr.
*Attorney, Agent, or Firm*—Nixon & Vanderhye

[57] ABSTRACT

Parasitic and viral diseases are treated with a pyrethroid preferably in the presence of alpha-pinene. Preferred compositions are extracts of pyrethrum with water, aqueous ethyl alcohol, or alpha-pinene.

11 Claims, No Drawings

PYRETHROID-CONTAINING PHARMACEUTICAL COMPOSITIONS,

This application is a continuation-in-part of U.S. application Ser. No. 595,360 filed Mar. 30, 1984, pending.

FIELD OF THE INVENTION

The present invention relates to the treatment of parasitic and, especially, viral diseases with a pyrethroid. It provides pyrethroids, and pharmaceutical compositions containing a pyrethroid, for treating a parasitic or viral disease. Further, it provides methods of treatment of a parasitic or viral disease by administering to a patient suffering said disease an effective amount of a pyrethroid.

BACKGROUND OF THE INVENTION

The pyrethroids include naturally occurring and synthetic esters of chrysanthemummonocarboxylic acid (i.e. 2,2-dimethyl-3-(2'-methylpropenyl)-cyclopropane-carboxylic acid) or chrysanthemumdicarboxylic acid (i.e. 2,2 -dimethyl-3-(2'-carboxypropenyl)- cyclopropane-carboxylic acid) and are widely used as insecticides. The most important naturally occurring pyrethroids are Pyrethrin I and II which are the major active insecticidal principles of pyrethrum. Pyrethrin I is the pyrethrolone (i.e. 4-hydroxy-3-methyl-2-(2',4'-pentadienyl)-2-cyclopenten-1-one) ester of chrysanthemummonocarboxylic acid and Pyrethrin II is the pyrethrolone 3-ester of chrysanthemumdicarboxylic acid-1-methyl ester. Pyrethrum also contains as minor active insecticidal principles Cinerin I and Cinerin II, which are the 4-hydroxy-3-methyl-2-(2'-butenyl)-2-cyclopenten-1-one esters of chrysanthemummonocarboxylic acid and chrysanthemumdicarboxylic acid-1-methyl ester respectively. Pyrethroids have low mammalian toxicity because they are relatively easily metabolized by warm-blooded animals and hence have found widespread acceptance as insecticides.

Some medical uses have been proposed for certain pyrethroids but, to the best of our knowledge, the majority of such uses have been directly related to their known insecticidal properties. The medical uses presently known to us are briefly acknowledged below.

Pyrethrum has been used as an active ingredient in an ointment for the treatment of scabies, which is a contagious skin infection caused by the mite Sarcoptes scaboi (see The Merck Index, Eighth Edition, 1968). Further, pyrethrum has been used in insect repellent creams (see the Extra Pharmacopoeia, Martindale, Twenty- fourth Edition, 1958) and in external preparations for the treatment of body lice, especially head lice (see "A 200 Pyrinate" and "Rid", The Physicians Desk Reference 1982). In this connection, UK Patent Specification No. 2072013 (published 1981) describes improving the activity of pyrethroids in the treatment of body lice by using them in conjunction with vegetable oils and/or detergents.

It has been proposed to use certain synthetic pyrethroids in the veterinary treatment of various forms of mange and ticks by oral, parenteral and topical routes (see US Pat. No. 4100297 issued 1978).

It was proposed in 1936 (see UK Patent Specification No. 447949) to use a pyrethrum containing composition in the treatment of gonorrhoea and dental suppurating diseases. The composition comprises a petroleum ether, or similar, extract of pyrethrum together with perilla aldehyde in an organic solvent. The perilla aldehyde was obtained from oil of perilla treated so as to eliminate limonene and pinene and other impurities. We understand that oil of perilla is obtained from a type of mint plant.

More recently (1959), it has been reported that pyrethrin extracts of Chrysanthemium cinerariaefolium have muscle relaxant properties as tested using guinea pig and rat ileum (see Chemical Abstracts, 53, 4570f).

Surprisingly, it has been found that pyrethroids are effective at low doses in the treatment of a wide range of parasitic and viral diseases in humans, including amoebiasis, genital herpes, hepatitis, influenza, malaria and parotitis (mumps).

SUMMARY OF THE INVENTION

According to a first aspect of the present invention, there is provided a pyrethroid for use in the treatment of a parasitic or viral disease.

According to a second aspect of the present invention there is provided a pharmaceutical composition for use in the treatment of a parasitic or viral disease, which composition comprises a pyrethroid in admixture or otherwise associated with a pharmaceutically acceptable diluent or carrier.

According to a third aspect of the present invention, there is provided a pharmaceutical composition in unit dosage form for the treatment of a parasitic or viral disease comprising a pyrethroid in admixture or otherwise associated with a pharmaceutically acceptable diluent or carrier and containing 0.0005 mg to 5 mg of the pyrethroid per unit dose.

According to a fourth aspect of the present invention, there is provided a method of treating a parasitic or viral disease which comprises administering to a patient suffering the disease, an effective amount of a pyrethroid.

DETAILED DESCRIPTION OF THE INVENTION

Pyrethroids are useful in the treatment of parasitic and viral diseases, especially, but not exclusively, amoebiasis, genital herpes, hepatitis, influenza, malaria and parotitis (mumps). Other parasitic diseases which are expected to respond to such treatment include trichuriasis, oxyuriasis, taenia, uncinariasis, ascariasis and trichomoniasis. Other viral diseases which are expected to respond to treatment with a pyrethroid include common cold, and herpes simplex and zoster infections. It has also been found that pyrethroids are useful as disinfectants for the treatment of infected wounds such as those caused by burns and physical injury and in the treatment of diabetic ulcers.

The pyrethroid can be any naturally occurring or synthetic ester of chrysanthemummonocarboxylic acid or chrysanthemumdicarboxylic acid which is non-toxic and otherwise pharmacologically acceptable at the dosages employed. However, the presently preferred pyrethroids for use in the present invention are those derived from pyrethrum, namely Cinerin I and II and, especially, Pyrethrin I and II. Pyrethrum itself can be used but it is presently especially preferred that the pyrethroid should be obtained by extracting pyrethrum with water, ethyl alcohol or, most preferred, with alpha-pinene. The alpha-pinene can be in the form of Mexican, or other, turpentine containing at least 80% alpha-pinene. Usually, the said preferred pyrethroid will be used in the form of a solution in water, aqueous alcohol or, especially, alpha-pinene.

In connection with the above, it appears that alpha-pinene exerts a synergistic effect on pyrethroids enhancing their activity in treating parasitic and viral diseases. Accordingly, it is a preferred feature of the present invention that alphapinene is administered concomitantly with the pyrethroid, advantageously in the same composition.

It is also preferred that an alkali metal bisulphite, especially sodium metabisulphite, is present in the composition of the invention.

It is particularly preferred that both alphapinene and the bisulphite are contained in the composition of the invention.

The pyrethroids can be administered in various manners to achieve the desired effect. They can be administered alone or in the form of pharmaceutical preparations to the patient being treated, preferably orally. The amount of compound administered will vary and can be any effective amount. Depending upon the patient, the pyrethroid, and the mode of administration, the quantity of pyrethroid administered may vary over a wide range to provide, for example, from about 0.0001 mg/kg to about 1 mg/kg, usually about 0.01 to about 0.1 mg/kg, of body weight of the patient per dose. Unit doses of pyrethroid can contain, for example, from about 0.0005 mg to about 5 mg, usually about 0.01 to about 1 mg, of the pyrethroid and may be administered, for example, from 1 to 4 times daily.

It will be appreciated that the dosage levels referred to above are substantially less than those envisaged in U.S. Pat. No. 4,100,297 for internal administration of certain pyrethroids for the treatment of acarids. The lowest dose specified in the U.S. patent is 3 mg/kg.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as one or more drops or a 5 ml (teaspoon) quantity of a liquid or a half or quarter of a scored tablet, of the multiple dose form.

In the composition aspect of the invention there are provided pharmaceutical compositions in which form the pyrethroids will normally be utilized. Such formulations are prepared in a manner well known per se in the pharmaceutical art and usually comprise at least one pyrethroid in admixture or otherwise in association with a pharmaceutically acceptable carrier or diluent therefor. For making those formulations the active ingredient usually will be mixed with a carrier, or diluted by a diluent, or enclosed or encapsulated in a capsule, sachet, cachet, paper or other container. The carrier or diluent may be solid, semi-solid or liquid material which serves as a vehicle, excipient or medium for the active ingredient. Suitable carriers or diluents are well known per se. As indicated above, it is presently preferred that the pyrethroid is administered as a solution in a suitable liquid carrier such as water or, preferably, aqueous alcohol or, especially, alphapinene. When administered as a solution, the concentration of pyrethroid usually will be in the range 0.001 to 1, especially 0.01 to 0.5, percent by weight based on the liquid carrier.

The compositions of the invention may be adapted for enteral or parenteral use and may be administered to the patient in the form of tablets, capsules, suppositories, solutions, suspensions or the like.

One preferred composition of the invention comprises a solution of 0.001 to 1.0, preferably 0.1 to 0.5, per cent by weight pyrethroid in alpha-pinene preferably containing up to 11% sodium metabisulphite. A particularly preferred example of said composition is obtained by macerating dried pyrethrum flowers for, for example, 30 days in Mexican turpentine optionally containing sodium metabisulphite and then filtering off the solids content.

Another preferred composition of the invention comprises a solution of 0.001 to 1.0, preferably 0.1 to 0.5, per cent by weight pyrethroid in aqueous ethyl alcohol preferably containing up to 11% sodium metabisulphite. Suitably, the aqueous alcohol contains 25 to 35% ethyl alcohol. A particularly preferred example of said composition is obtained by homogenizing an ethyl alcohol extract of dried pyrethrum flowers with aqueous ethyl alcohol optionally in the presence of sodium metabisulphite.

The invention is further illustrated in the following Examples.

EXAMPLE 1

Mexican gum turpentine (specific weight 860.5, 80% minimum alpha-pinene content) (1 litre) is slowly added to a sodium metabisulphite (105 gms) in a 1.5 litre vessel. The vessel is closed and stirred gently for 10 minutes. Chrysanthemum powder (110 gms, 1.2% concentration) is added and the mixture stirred every 6 days. The mixture is left to macerate for 30 days with occasional stirring and then the solids filtered off. The filtrate (identified as "V-1") is stored in dropper bottles for administration at a dose of 1 drop orally per 10 kg body weight of patients suffering from a parasitic or viral infection.

V-1 has been found to be effective against type A hepatitis (infectious hepatitis) and type B hepatitis (serum hepatitis) at doses of 1 drop orally per 10 kg body weight twice daily. A clinic treated 7 cases of acute hepatitis in patients in which the main symptoms and signs were anorexia, extreme fatigue (which made it impossible to attend school or work), moderate temperature (38° C.), cephalalgia and poor condition in the hepatic area, choluria, hepatomegaly, icteric conjunctivitis, hypocholia, acholia, splenamegaly and ascites. In laboratory tests, bilirubin, glutaminase and oxalacetic, alkaline phosphatase, lactic dehydrogenase quantities were considerably increased. The patients were given V-1, in relation to their weight and their symptoms and signs diminished gradually until complete recovery after 10 to 12 days.

The clinic also successfully treated 2 cases of chronic hepatitis caused by type B virus. One was a boy, age 5, who presented most of the symptoms and signs above stated as well as the altered laboratory tests. In this case 25 days were needed for complete recovery.

Sample clinical results of treatment of hepatitis with V-1 are provided in Example 4.

Further, the clinic successfully treated amoebiasis; genital herpes, and malaria with V-1 and sample clinical results are provided in Examples 2, 5 and 3 respectively.

It has also been found that V-1 is useful as a disinfectant agent. The clinic had experience with various patients who presented infected wounds produced by burns, diabetic ulcers and pistol wounds. V-1 was used applied directly to the wound and complete recovery was achieved in a matter of a week to a month, depending on the case.

EXAMPLE 2

SAMPLE CLINICAL RESULTS (V-1) - AMOEBIASIS

PATIENT 2A
Male:
Age: 6 years
Weight: 20 Kgs.
Temperature: 36.5° C.
Principal symptoms and signs:
Anorexia, sometimes shivering fits and general feeling of illness which could be defined with precision. Thereafter there were diarrhoeial evaculations with mucus, blood and very foetid odour in great quantity and with a frequency of 4 evacuations per day. This continued for 3 days, appeared again in 8 days with the evacuations having the same characteristics as described above and accompanied, on some occasions, by a fever of 38° C., nausea and vomiting of the gastric contents. Patient referred to abdominal pain upon touching and where there was slight abdominal distention.
Diagnosis
Acute intestinal amoebiasis
Treatment
5 drops V-1 orally twice a day
Result
Complete recovery after 10 days treatment.
PATIENT 2B
Male:
Age: 6 years
Weight: 19 Kgs.
Temperature: 36.5° C.
Principal symptoms and signs:
The patient complained of cramp pains localized in the left iliac fossa, painful to the touch, flatulence, and with disorders of the intestinal evacuations, which then were presented in the form of diarrhoeia with mucus and sometimes blood preceded by tenesmus, with a frequency of 4 to 5 times per day. These evacuations lasted 3 days and returned each 8 days having the same characteristics as set out above.
Diagnosis:
Acute intestinal amoebiasis.
Treatment
5 drops V-1 orally twice a day
Result
Complete recovery after 8 days treatment.
PATIENT 2C
Male:
Age: 35 years
Weight: 70 Kgs.
Temperature: 36.5° C.
T.A.: 140/80
Principal symptoms and signs:
Diarrhoeial evacuations, intestinal colic, nausea, vomiting and rectal tenesmus which accompanied defecation. The patient displayed anorexia and shivering fits and this condition lasted from 3 to 5 days with renewed appearance of intestinal colic with pasty evacuations, semiliquid, of foetid smell, with mucous and sometimes with blood and remains of intestinal mucous and which was accompanied by rectal tenesmus having a frequency of 6 to 8 evacuations per day. Generally poor state, anorexia, asthenia and acratia.
Diagnosis
Acute intestinal amoebiasis.
Treatment
8 drops V-1 orally three times a day
Result
Complete recovery after 15 days treatment.
PATIENT 2D
Female:
Age: 6 years
Weight: 21 Kgs.
Temperature: 36.5° C.
Principal symptoms and signs:
Anorexia, nausea, and sometimes vomiting with diarrhoeial evacuations which were abundant and semi-liquid and were accompanied by blood and with a frequency of 6 times per day. The evacuations lasted 4 days on average and were repeated each 3 days becoming more intense and accompanied by abdominal pain.
Diagnosis
Acute intestinal amoebiasis.
Treatment
5 drops V-1 orally twice a day.
Result
Complete recovery after 7 days treatment.
PATIENT 2E
Male:
Age: 4 years
Weight: 16 Kgs.
Temperature: 36.5° C.
Principal symptoms and signs:
Intestinal colic, nausea, and sometimes vomiting preceded by semiliquid diarrhoeial evacuations, of pasty form and with mucous and with remains of food and which were accompanied by rectal tenesmus and with a frequency of 5 evacuations per day. Further, he was generally in poor condition with anorexia, asthenia and acratia.
Diagnosis
Acute intestinal amoebiasis.
Treatment
5 drops V-1 orally twice a day.
Result
Complete recovery after 8 days treatment.
PATIENT 2F
Male:
Age: 4 years
Weight: 16 Kgs.
Principal symptoms and signs:
The patient had anorexia, asthenia, and slight acratia and there were diarrhoeial evacuations with mucus, blood and the remains of food, accompanied by tenesmus and presented with a frequency of 4 evacuations per day which lasted 3 days, repeated in 5 days with the same characteristics as noted above. Abdominal distention and pain upon touching the left iliac fosse.
Diagnosis
Acute Intestinal amoebiasis
Treatment
5 drops V-1 orally twice a day.
Result
Complete recovery after 7 days treatment

EXAMPLE 3

SAMPLE CLINICAL REPORTS (V-1)-MALARIA
PATIENT 3A

Male:
Age: 30 years
Weight: 70 Kgs.
T.A.: 120/70
Temperature: 38° C.
Principal symptoms and signs:
Fever of 38° to 39° C. with general poor condition, with asthenia, acratia and anorexia, and with loss of weight (unquantified). Slight diaphoresis, intense frontal Cephalalgia and extreme debility. Hepatomegalia Grade 2 painfull to the touch and slight splenomegalia +. The patient complained of myalgia and arthrosis of variable intensity.
Diagnosis
Malaria
Treatment
8 drops V-1 orally twice a day
Result
Complete recovery after 8 days treatment.

PATIENT 3B
Male:
Age: 32 years
Weight: 76 Kgs.
T.A.: 130/70
Temperature: 39° C.
Principal symptoms and signs:
Intermittent fever preceded by intense shivering fits which from time to time shook the patient and the duration of which was approximately from 4 to 6 hours. Intense cephalalgia which did not cease with treatment with analgesics, tachycardia, oliguresis and dry mouth. Hepatomegalia ++, anaemia Grade 1 and slight splenomegalia.
Diagnosis
Malaria
Treatment
8 drops V-1 orally twice a day
Result
Complete recovery after 12 days treatment.

PATIENT 3C
Male:
Age: 30 years
Weight: 69 Kgs.
T.A.: 140/80
Temperature: 39° C.
Principal symptoms and signs:
Intermittent fever (unquantified) preceded by intense shivering fits, the mean duration of which was 8 hours approximately and which disappeared in the form of intense diaforesis. Hypothermia, intense frontal cephalalgia, arthralgia, anorexia, asthenia and acratia accompanied by loss of weight (unquantified).
Diagnosis
Malaria
Treatment
8 drops V-1 orally twice a day
Result
Complete recovery after 8 days treatment.

PATIENT 3D
Male:
Age: 52 years
Weight: 77 Kgs.
T.A.: 150/80
Temperature: 39° C.
Principal symptoms and signs:
Intermittent fever (unquantified) precided by shivering fits, the mean duration of which was three hours after which they disppeared in the form of intense diaforesis. Hypothermia, cephalalgia, thirst, asthenia, and acratia. Anaemia grade 1, hepatomegalia ++, splenomegalia+which were painful to the touch. The skin of the patient was dry and hot, with reddening of the face and with very high temperatures (up to 40° C.) General poor condition accompanied by intense fatigue and debili0 7ty.
Diagnosis
Malaria
Treatment
8 drops V-1 orally twice a day
Result
Complete recovery after 15 days treatment.

PATIENT 3E
Male:
Age: 38 years
Weight: 77 Kgs.
T.A.: 130/90
Temperature: 39° C.
Principal symptoms and signs:
Intermittent fever accompanied by intense shivering fits with a duration of approximately 6 hours and which disappeared in the form of diaphoresis which was very intense and which from time to time led to saturation of the clothing of the patient, and which left the patient without symptoms and very debilitated. The fever occurred the following day and reached 40° C. and was accompanied by intense cephalalgia, myalgia, arthralgia, oliguresis and bad general state.
Diagnosis
Malaria
Treatment
9 drops V-1 orally twice a day
Result
Complete recovery after 20 days treatment.

EXAMPLE 4

SAMPLE CLINICAL RESULTS - HEPATITIS

PATIENT 4A
Male:
Age: 30 years
Weight: 63 Kgs.
T.A.: 110/70
Temperature: 39° C.
Principal symptoms and signs:
Alcoholism since 18 years of age (taken twice a week to achieve complete intoxication). Anorexia, generally poor condition, vomiting of the contents of the stomach during which there appeared joint pains of variable intensity which are accompanied by choluria and acholia. This condition lasted three days and was followed by generalized icteric conjunctivitis ++. Generalized abdominal pain, as well as hepatomegalia Grade ++, and abdominal distention. Fever 39° C., with Asthenia, acratia and anorexia.
Diagnosis
Acute (infectious) Viral Hepatitis.
Treatment
7 drops V-1 orally twice a day
Result
Complete recovery after 21 days treatment.

PATIENT 4B

| Female: | Age: 5 years |
| Weight: 18 Kgs. | Temperature: 38° C. |

Principal symptoms and signs:

From three years of age had diarrhoeial evacuations with mucus and blood with a frequency of twice per week. Anorexia, asthenica, and acratia which was accompanied by cephalalgia, a fever of 38° C. and generally poor condition which lasted three days after which there appeared choluria, hypocholia and acholia, as well as icteric conjunctivities. Slight hepatomegalia +and slight splenomegalia +. Fever at 38° C., asthenia, acratia, anorexia which was accompanied by attacks on the general health.

| Bilirubina: | |
|---|---|
| direct | 6 mg/100 ml |
| indirect | 5 mg/100 ml |
| lactic dehydrogenase | 815 mU/ml |
| Transaminase: | |
| glutamic - pyruvic | 22 mU/ml |
| glutamic - oxalacetic | 26 mU/ml |
| alkaline phosphatase | 213 mU/ml |

Diagnosis
Viral hepatitis, type "A"
Treatment
7 drops V-1 orally twice a day
Result
Complete recovery after 15 days treatment.
PATIENT 4C

| Male: | Age: 8 years |
|---|---|
| Weight: 24 Kgs. | Temperature: 38° C. |

Principal symptoms and signs:

Anorexia, moderate fever of 38° C., Cephalalgia and generally poor condition which was accompanied by muscular pains. After three days there appeared choluria and icteric conjunctivitis accompanied by acholia and hypocholia. Abdominal distention +, hepatomegalia painful to the touch ++, and slight splenomegalia. In laboratory examination the total amount of seral bilirubin was increased. Fever of 38° C., cephalia, anorexia, asthenia and acratia.

| Bilirubin: | |
|---|---|
| direct | 3.5 mg/100 ml |
| indirect | 2 mg/100 ml |
| lactic dehydrogenase | 467 mU/ml |
| Transaminase: | |
| glutamic - pyruvic | 78 mU/ml |
| glutamic - oxalacetic | 52 mU/ml |
| alkaline phosphatase | 174 mU/ml |

Diagnosis
Viral hepatitis, type "A" (Infectious)
Treatment
5 drops V-1 orally twice a day
Result
Complete recovery after 15 days treatment.
PATIENT 4D

| Male: | Age: 53 years | |
|---|---|---|
| Weight: 72 Kgs. | Temperature: 37.5° C. | T.A. 140/80 |

Principal symptoms and signs:

Cephalalgia arteriomuscular pains and generalized urticaria which lasted 10 days, to present choluria which was accompanied by icteric conjunctivitis, hypocholic and acholic. Hepatomegaly painful to the touch ++, and slight splenamegaly. The amount of bilirubin as well as transaminase were altered. Generally poor condition, asthenia, acratia and anorexia.

| Bilirubin: | |
|---|---|
| direct | 7.3 mg/100 ml |
| indirect | 5.2 mg/100 ml |
| lactic dehydrogenase | 684 mU/ml |
| Transaminase: | |
| glutamic - pyruvic | 68 mU/ml |
| glutamic - oxalacetic | 57 mU/ml |
| alkaline phosphatase | 148 mU/ml |

Diagnosis
Viral hepatitis, type "B"
Treatment
10 drops V-1 orally twice a day Result
Complete recovery after 20 days treatment.
PATIENT 4E
Male:
Age: 6 years
Weight: 21 Kgs.
Clinical Diagnosis
Viral Hepatitis.
Treatment
4 drops V-1 orally three times daily.
Result
Complete recovery after 22 days treatment.
PATIENT 4F
Male:
Age: 45 years
Weight: 80 kgs
Clinical Diagnosis
Viral Hepatitis
Treatment
8 drops V-1 orally three times daily
Result
Complete recovery after 16 days treatment.
PATIENT 4G
Female:
Age: 31 years
Weight: 56 Kgs.
Clinical Diagnosis
Viral Hepatitis.
Treatment
6 drops V-1 orally three times daily.
Result
Complete recovery after 22 days treatment.

EXAMPLE 5

SAMPLE CLINICAL RESULTS (V-1) GENITAL HERPES

PATIENT 5A
Male:
Age: 26 years
Weight: 65 Kgs.
Clinical Diagnosis
Genital Herpes
Treatment
10 drops V-1 orally three times daily.
Result
Complete recovery after 40 days treatment leaving no scars or marks.
PATIENT 5B
Female:
Age: 32 years Weight: 65 Kgs.
Clinical Diagnosis
Genital Herpes
Treatment
10 drops V-1 orally three times daily.
Result
Complete recovery after 38 days treatment leaving no scars or marks.
PATIENT 5C
Male:
Age: 31 years
Weight: 70 Kgs.
Clinical Diagnosis
Genital Herpes
Treatment
10 drops V-1 orally three times daily.
Result
Complete recovery after 40 days treatment leaving no scars or marks.
PATIENT 5D
Male:
Age: 30 years
Weight: 76 Kgs.
Clinical Diagnosis
Genital Herpes
Treatment
11 drops V-1 orally three times daily.
Result
Complete recovery after 42 days treatment leaving no scars or marks.
PATIENT 5E
Female:
Age 25
Weight: 58 Kgs.
Clinical Diagnosis
Genital Herpes
Treatment
9 drops V-1 orally three times daily.
Result
Patient attended at clinic on following days:
Day 1—Treatment commenced
Day 7—No improvement
Day 14—No improvement
Day 21—Wounds decreased in size
Day 28—Wounds healing
Day 42—Wounds greatly improved and healing rapidly.
Day 53—Wounds completely dry and without so treatment ceased.
PATIENT 5F
Male:
Age: 30 years
Weight: 70 Kgs.
Clinical Diagnosis
Genital Herpes
Treatment
10 drops V-1 orally three times daily.
Result
Patient attended at clinic on following days:
Day 1—Treatment commenced
Day 7—No improvement
Day 14—No improvement
Day 21—No improvement
Day 28—No improvement
Day 42—Wounds healing rapidly.
Day 53—Wounds completely dry and treatment ceased.
PATIENT 5G
Male:
Age: 28 years
Weight: 64 Kgs.
Clinical Diagnosis
Genital Herpes
Treatment
7 drops V-1 orally three times daily plus direct application of V-1 to affected area every 12 hours.
Result
Complete recovery after 35 days treatment leaving no scars or marks
PATIENT 5H
Female:
Age: 20 years
Weight: 48 kgs.
Clinical Diagnosis
Genital Herpes
Treatment
5 drops V-1 orally three times daily plus direct application of V-1 to affected area every 12 hours.
Result
Complete recovery after 35 days treatment leaving no scars or marks.
PATIENT 5I
Male:
Age: 35 years
Weight: 70 Kgs.
Clinical Diagnosis
Genital Herpes
Treatment
7 drops V-1 orally three times daily plus direct application of V-1 to affected area every 12 hours.
Result
Complete recovery after 20 days treatment leaving no scars or marks.
PATIENT 5J
Female:
Age: 26 years
Weight: 54 Kgs.
Clinical Diagnosis
Genital Herpes
Treatment
6 drops V-1 orally three times daily plus direct application of V-1 to affected area every 12 hours.
Result
Complete recovery after 20 days treatment leaving no scars or marks.

All of Patients 5A to 5J were checked every 14 days for two months following end of treatment and in all cases there was no sign of return of infection.

EXAMPLE 6

Water (650 ml) is added to sodium metabisulfite (68 gms) in a 1.5 liter vessel. The vessel is closed and the mixture stirred for 10 minutes. In a separate 1 liter vessel, chrysanthemum powder (110 gms; 1.2% concentration) is added to ethyl alcohol (180 proof; 350 ml) and the mixture stirred every six days. The mixture is allowed to macerate for 30 days at room temperature and then filtered. The filtrate (identified as "V-2" has similar medical properties to those of "V-1" but is somewhat less active.

EXAMPLE 7

SAMPLE CLINICAL RESULTS (V-2) - GENITAL HERPES

PATIENT 7A

Female:
Age: 26 years
Weight: 51 Kgs.
Clinical Diagnosis
Genital Herpes
Treatment
8 drops V-2 orally three times daily
Result
Wounds completely dry after 43 days treatment.
PATIENT 7B
Male:
Age: 21 years
Weight: 68 Kgs.
Clinical Diagnosis
Genital Herpes
Treatment
10 drops V-2 orally three times daily
Result
Wounds completely dry after 20 days treatment.
PATIENT 7C
Female:
Age: 19
Weight: 46 Kgs.
Clinical Diagnosis
Genital Herpes
Treatment
7 drops V-2 orally three times daily
Result
Wounds completely dry after 28 days treatment.
PATIENT 7D
Male:
Age: 33 years
Weight: 72 Kgs.
Clinical Diagnosis
Genital Herpes
Treatment
11 drops V-2 orally twice daily
Result
Wounds completely healed without scar after 40 days treatment.
PATIENT 7E
Female:
Age: 25 years
Weight: 55 Kgs.
Clinical Diagnosis
Genital Herpes
Treatment
9 drops V-2 orally twice daily
Result
Wounds completely healed with no scar after 40 day treatment.
PATIENT 7F
Female:
Age: 18 years
Weight: 52 Kgs.
Clinical Diagnosis
Genital Herpes
Treatment
8 drops V-2 orally three times daily.
Result
Patient attended at clinic on following days:
Day 1—Treatment commenced
Day 7—No improvement
Day 15—No improvement
Day 22—No improvement
Day 29—No improvement
Day 36—No improvement
Day 43—Wounds healing
Day 57—Wounds completely dry
Day 71—No sign of herpetic injury and treatment ceased.
PATIENT 7G
Male:
Age: 22 years
Weight: 68 Kgs.
Clinical Diagnosis
Genital Herpes
Treatment
10 drops V-2 orally three times daily.
Result
Patient attended at clinic on following days:
Day 1—Treatment commenced
Day 7—No improvement
Day 15—No improvement
Day 22—No improvement
Day 29—Wounds decreased in size, form and sensitivity
Day 36—No further improvement
Day 43—No further improvement
Day 57—Wounds completely dry
Day 71—No sign of herpetic injury and treatment ceased.

All of patients 7A to 7G were checked every 14 days for two months following end of treatment and in all cases there was no sign of return of infection.

EXAMPLE 8

SAMPLE CLINICAL RESULT (V-2) - VIRAL HEPATITIS

PATIENT 8
Male:
Age: 18 years
Weight: 65 Kgs.
Clinical Diagnosis
Viral Hepatitis
Treatment
7 drops V-2 orally three times daily.
Result
Complete recovery after 16 days treatment.

EXAMPLE 9

SAMPLE CLINICAL RESULTS (V-1) - VIRAL INFLUENZA

PATIENT 9A
Male:
Age: 28 years
Weight: 68 Kgs.
Clinical Diagnosis
Viral Influenza
Treatment
7 drops V-1 orally three times daily after meals.
Result
Complete recovery after 3 days.
PATIENT 9B
Female:
Age: 54 years
Weight: 60 Kgs.
Clinical Diagnosis
Viral Influenza
Treatment
6 drops V-1 orally three times daily after meals.
Result
All symptoms disappeared after three days treatment.
PATIENT 9C
Male:

Age: 8 years
Weight: 26 Kgs.
Clinical Diagnosis
Viral Influenza
Treatment
3 drops V-1 orally three times daily after meals.
Result
All symptoms disappeared after 2 days treatment.
PATIENT 9D
Female:
Age: 30 years
Weight: 58 Kgs.
Clinical Diagnosis
Viral Influenza
Treatment
6 drops V-1 orally three times daily after meals.
Result
All symptoms disappeared after two days treatment.

EXAMPLE 10

SAMPLE CLINICAL RESULTS (V-1) - PAROTITIS

PATIENT 10A
Male:
Age: 40 years
Weight: 62 Kgs.
Clinical Diagnosis
Parotitis
Treatment
7 drops V-1 orally three times daily.
Result
Complete recovery after 13 days treatment.
PATIENT 10B
Male:
Age: 18 years
Weight: 60 Kgs.
Clinical Diagnosis
Parotitis
Treatment
6 drops V-1 orally three times daily.
Result
Complete recovery after 8 days treatment.

EXAMPLE 11

SAMPLE CLINICAL RESULTS (V-2) - PAROTITIS

PATIENT 11A
Male:
Age: 54 years
Weight: 75 Kgs.
Clinical Diagnosis
Parotitis
Treatment
8 drops V-2 orally three times daily.
Result
Complete recovery after 7 days treatment.
PATIENT 11B
Female:
Age: 60 years
Weight: 71 Kgs.
Clinical Diagnosis
Parotitis
Treatment
7 drops V-2 orally three times daily.
Result
Complete recovery after 13 days treatment.

EXAMPLE 12

SAMPLE CLINICAL RESULT (V-1) - HERPES ZOSTER

PATIENT 12
Male:
Age: 58 years
Weight: 78 Kgs.
Clinical Diagnosis
Herpes Zoster infection having small (1-5 mm) red blisters in the intercostal region grouped in the form of an erythema. Intense pain at palpation, paresthesia, cutaneous hiperesthesia and itching.
Treatment
8 drops V-1 orally three times daily plus direct application of V-1 in affected area every twelve hours.
Result
Complete recovery after 37 days treatment.

EXAMPLE 13

SAMPLE CLINICAL RESULT (V-2) - POST VIRAL SYNDROME

PATIENT 13
Female:
Age: 42 years
Weight: 56 Kgs.
Clinical Diagnosis
Post Viral Syndrome
Treatment
6 drops of V-2 every 12 hours for 15 days
Result
A 42-year-old woman, height 5 feet 6 inches, weight 56 Kilos, suffered many of the symptoms of post viral syndrome, which consisted of body tremor, loss of weight, hypotention, organic depression, strong body odor, allergy to a great number of foods, lack of energy, cardiac arrhythmia, pain in the spinal column, aphasia, nausea, dizziness, episodes of rage and panic attacks.
She was seen by many physicians in Mexico and the U.S., but nothing organically wrong was noted except for an extremely low immunological response to allergic test. This assertion was denied, though, at the Immunological Department of Rush Presbyterian, St. Lukes Medical Center, in Chicago, where she was told that she could have a post viral syndrome. Aspirin was prescribed as a vasodilator, but all the symptoms remained.
Six drops of V-2 every 12 hours were prescribed for a period of 15 days, after which her symptoms disappeared and a swelling about the size of one-half of an orange formed at the base of the spine, which also disappeared in the course of the week.
After 3 years of this treatment, mild symptoms have recurred, but the patient says that she has recovered 90% of her cognitive functions.

EXAMPLE 14

SAMPLE CLINICAL RESULT (V-2) - UNDIAGNOSED SYMPTOMS

PATIENT 14
Female:
Age: 19 years
Weight: 54 Kgs.
Clinical Diagnosis
Symptoms: body tremor, loss of weight, hypotention, lack of energy, pain in the spinal column, panic attacks, dizziness and bizarre thoughts. Nothing organically wrong detected.

Treatment 6 drops of V-2 every 12 hours for 15 days

Result

A 19-year-old single woman, height 5 feet 8 inches, weight 54 Kilos, suffered the symptoms listed above. She was seen by physicians in Mexico and in Temple, Texas, who could not find anything organically wrong with her. Some physicians suggested her symptoms could be of psychological origin.

The patient was given 6 drops of V-2 every 12 hours for a period of 15 days, after which her symptoms disappeared completely. After three years of this treatment, this young woman is in excellent physical condition.

EXAMPLE 15

SAMPLE CLINICAL RESULT (V2) - MONONUCLEOSIS

PATIENT 15

Female:

Age: 44 years

Weight: 60 Kgs.

Clinical Diagnosis

Symptoms of Mononucleosis

Treatment 6 drops of V-2 every 12 hours for 60 days

Result

A 44-year-old married woman, height 5 feet 4 inches, weight 60 Kilos, had suffered intermittently for the last 20 years the symptoms of mononucleosis including fever, sore throat, swelling of the lymph glands, high white blood cell count, lack of energy and depression. Symptoms were more pronounced following long trips or extended periods of physical activity. She started to take 6 drops of V-2 every 12 hours for 60 days, and she has not had any symptoms in the last two years.

I claim:

1. A method of treating a viral disease which comprises administering to a patient suffering the disease, an effective amount of a non-toxic, pharmaceutically acceptable pyrethroid selected from the group consisting of an ester of chrysanthemummonocarboxylic acid, an ester of chrysanthemumdicarboxylic acid, pyrethrum, Cinerin I, Cinerin II, Pyrethrin I and Pyrethrin II.

2. The method claimed in claim 1 wherein an activity enhancing amount of alpha-pinene is administered concomitantly with the pyrethroid.

3. The method claimed in claim 1 wherein the pyrethroid is administered at a dose in the range 0.0001 mg/kg to 1 mg/kg body weight one to four times daily.

4. The method as claimed in claim 3 wherein the pyrethroid is administered at a dose in the range 0.01 to 0.1 mg/kg body weight one to four times daily.

5. The method claimed in claim 1, wherein the pyrethroid is selected from the group consisting of an extract of pyrethrum with water, an extract of pyrethrum with ethyl alcohol, and an extract of pyrethrum with alphapinene.

6. The method as claimed in claim 1 wherein the viral disease is genital herpes, viral hepatitis, viral influenza, or parotitis.

7. The method as claimed in claim 1 wherein the viral disease is herpes simplex or herpes zoster.

8. A method of treating post-viral syndrome comprising administering to a patient suffering the syndrome an effective amount of a non-toxic, pharmaceutically acceptable pyrethroid selected from the group consisting of an ester of chrysanthemummonocarboxylic acid, an ester of chrysanthemumdicarboxylic acid, pyrethrum, Cinerin I, Cinerin II, Pyrethrin I and Pyrethrin II, the pyrethroid administered at a dose in the range of 0.0001 mg/kg to 1 mg/kg body weight one to four times daily.

9. The method as claimed in claim 8 in which an activity-enhancing amount of alpha-pinene is administered concomitantly with the pyrethroid.

10. The method as claimed in claim 8 wherein the pyrethroid is administered at a dose in the range 0.01 to 0.1 mg/kg body weight one to four times daily.

11. The method claimed in claim 8 wherein the pyrethroid is selected from the group consisting of an extract of pyrethrum with water, an extract of pyrethrum with ethyl alcohol, and an extract of pyrethrum with alpha-pinene.

* * * * *